United States Patent
Penna (10) Patent No.: US 9,022,274 B2
(45) Date of Patent: May 5, 2015

(54) CIRCULAR STAPLER WITH INCREASED LUMEN DIAMETER

(75) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 660 days.

(21) Appl. No.: 13/397,039

(22) Filed: Feb. 15, 2012

(65) Prior Publication Data

US 2013/0206816 A1 Aug. 15, 2013

(51) Int. Cl.
*A61B 17/115* (2006.01)
*A61B 17/068* (2006.01)
*A61B 17/072* (2006.01)

(52) U.S. Cl.
CPC ............. *A61B 17/115* (2013.01); *A61B 17/068* (2013.01)

(58) Field of Classification Search
CPC ........... A61B 17/07207; A61B 17/115; A61B 17/072; A61B 17/1155; A61B 17/068; A61B 2017/07214
USPC .................. 227/175.1, 176.1, 179.1; 128/898
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

European Search Report dated Sep. 30, 2013 in European Application No. 13 15 5169.

*Primary Examiner* — Michelle Lopez (57) ABSTRACT

A surgical stapling device is provided having a shell assembly including an outer housing portion having areas of varying wall thicknesses. Individual staple pockets in a row of staple pockets are positioned in areas of thinner wall thicknesses. Areas of increased wall thicknesses form longitudinally extending strengthening ribs along an inner surface of the outer housing portion. The longitudinally extending strengthening ribs may be solid, indented in the wall of the outer housing portion and or bisected by a slot extending through the outer housing portion.

16 Claims, 8 Drawing Sheets

(56) References Cited

U.S. PATENT DOCUMENTS

| | | |
|---|---|---|
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |

(56) References Cited

U.S. PATENT DOCUMENTS

| | | |
|---|---|---|
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,907 B2 | 7/2008 | Racenet et al. |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |

(56) References Cited

U.S. PATENT DOCUMENTS

| | | |
|---|---|---|
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,146,790 B2 | 4/2012 | Milliman |
| 2003/0111507 A1 | 6/2003 | Nunez |
| 2005/0051597 A1 | 3/2005 | Tolendano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0012641 A1 | 1/2012 | Milliman et al. |
| 2012/0080492 A1 | 4/2012 | Scirica et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2 524 656 | 11/2012 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| WO | WO 8706448 A1 | 11/1987 |
| WO | WO 8900406 A1 | 1/1989 |
| WO | WO 9006085 A1 | 6/1990 |

CIRCULAR STAPLER WITH INCREASED LUMEN DIAMETER

BACKGROUND

1. Technical field

The present disclosure relates generally to a surgical stapling device for applying surgical staples to body tissue. More particularly, the present disclosure relates to a surgical stapling device suitable for performing circular anastomosis to hollow tissue organs.

2. Background of Related Art

Anastomosis is the surgical joining of separate hollow organ sections. Typically, an anastomosis procedure follows a procedure in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is concurrently advanced to core tissue of the hollow organ to free a tubular passage within the organ.

There is a desire to prevent stenosis, the incidence of strictures, improve the passage of material through the anastomosis site after surgery, and generally to form an anastomosis with an increased inner diameter.

SUMMARY

There is disclosed a surgical stapling device for stapling together a pair of tubular tissue sections while maximizing a resultant internal lumen formed between the pair of tubular tissue sections. The surgical stapling device generally includes a handle assembly having a firing trigger and a body portion extending distally from the handle assembly. A head portion is disposed adjacent the body portion and includes an anvil assembly and a shell assembly. The anvil assembly is movable in relation to the shell assembly between spaced and approximated positions. The shell assembly includes an outer housing portion having a wall including areas of thinner and thicker wall thicknesses and an outer line of staple pockets. Individual staple pockets in the outer line of staple pockets are positioned in areas of thinner wall thicknesses.

The outer housing portion is cylindrical and the outer line of staple pockets is an outer row of staple pockets. The areas of thicker wall thicknesses form longitudinally extending ribs extending along an inner surface of the wall of the outer housing portion. In one embodiment, the ribs are solid. In a more specific embodiment, the ribs are formed integrally with the wall of the outer housing portion. In an alternative embodiment, the ribs are indented in the wall of the outer housing portion. In a further alternative embodiment, the ribs are bisected by a slot and the slot extends through the ribs and the wall of the outer housing portion. In another embodiment, the ribs include angled sidewalls such that the ribs taper inwardly away from the inner surface of the wall of the outer housing portion.

There is also disclosed a surgical stapling device having a handle assembly including a firing trigger and a body portion extending distally from the handle assembly. A head portion is disposed adjacent the body portion and includes an anvil assembly and a shell assembly. The anvil assembly is movable in relation to the shell assembly between spaced and approximated positions. The shell assembly includes a cylindrical outer housing portion having a wall including areas of thinner and thicker wall thicknesses and an outer row of staple pockets, each staple pockets of the outer row of staple pockets being positioned in an area of thinner wall thickness.

A pusher back is movably mounted within the cylindrical outer housing portion for simultaneously driving staples contained within each of the staple pockets out of the staple pockets and into the anvil assembly. The pusher back includes longitudinally extending slots to accommodate the areas of thicker wall thicknesses.

The areas of thicker wall thicknesses form longitudinally extending ribs extending along an inner surface of the wall of the outer housing portion. In one embodiment, the ribs are solid. In an alternative embodiment the ribs are indented in the wall of the outer housing portion. In a further alternative embodiment, the ribs are bisected by one or more slots.

There is further disclosed a method of increasing the lumen diameter of a pair of stapled tubular tissue sections. The method includes providing an outer housing portion of a surgical stapling device having areas of increased and decreased wall thicknesses and positioning a row of staple containing pockets adjacent the areas of decreased wall thickness.

The outer housing portion of the surgical stapling device is positioned within a first tubular tissue section and an anvil member associated with the outer housing portion of the surgical stapling device is positioned within a second tubular tissue section.

The first tubular tissue section is approximated adjacent the second tubular tissue sections and staples are driven out of the staple containing pockets through the first and second tubular tissue sections and into the anvil member.

The areas of increased and decreased wall thickness of the outer housing portion includes longitudinally extending ribs formed along an inner surface of the outer housing portion.

The method further includes the step of severing excess tubular tissue with a cylindrical knife blade located adjacent the row of staple containing pockets.

DESCRIPTION OF THE DRAWINGS

An embodiment of the presently disclosed circular stapling device with increased lumen diameter is disclosed herein with reference to the drawings, wherein.

DETAILED DESCRIPTION OF EMBODIMENT

An embodiment of the presently disclosed surgical stapling device configured and dimensioned to form an anastomosis with an increased lumen diameter will now be described in detail with reference to the drawings wherein like numerals designate identical or corresponding elements in each of the several views. As is common in the art, the term 'proximal' refers to that part or component closer to the user, i.e. surgeon or physician, while the term "distal" refers to that part or component further away from the user.

Figure 1:
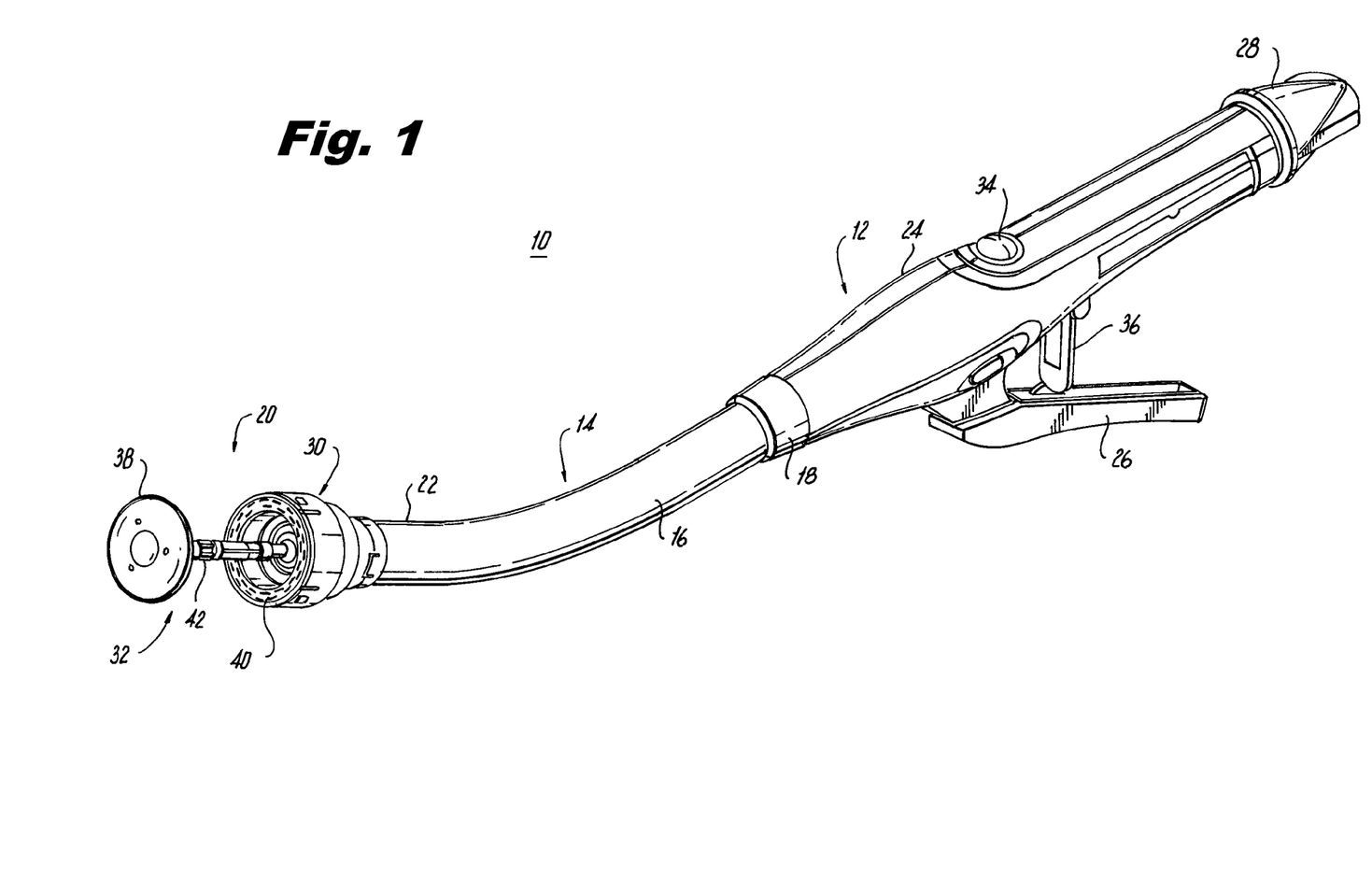
FIG. 1 is an enlarged perspective view of a circular stapling device having an increased lumen diameter.

Referring initially to FIG. 1, there is illustrated an embodiment of the presently disclosed surgical stapling device 10. Surgical stapling device 10 generally includes a handle assembly 12, an elongated body portion 14 having an elongated outer tube 16 extending distally from a distal end 18 of handle assembly 12, and a distal head portion 20 mounted on a distal end 22 of elongated outer tube 16. Handle assembly 12 includes a stationary portion 24 and a firing trigger 26 movably mounted on stationary portion 24 and a rotatable approximation knob 28. Surgical stapling device 10 includes internal components and functions substantially similar to that disclosed in U.S. Pat. No. 7,857,187, the entire disclosure of which is incorporated by reference herein.

Distal head portion 20 includes a shell assembly 30 mounted on distal end 22 of elongated outer tube 16 and an anvil assembly 32 movable relative to shell assembly 30 to capture tissue sections to be stapled there between. Anvil assembly 23 is movable, in response to rotation of approximation knob 28, between an open position spaced from shell assembly 30 to a closed position substantially adjacent shell assembly 30 for engaging and stapling tissue. An indicator 34 is provided on stationary portion 24 to give the user a visual indication of the position of anvil assembly 32 relative to shell assembly 30 to ensure tissue is properly clamped prior to stapling. A lock lever 38 is pivotally mounted on stationary portion 24 and is engagable with firing trigger 26 to prevent premature firing of surgical stapling device 10.

Figure 2:
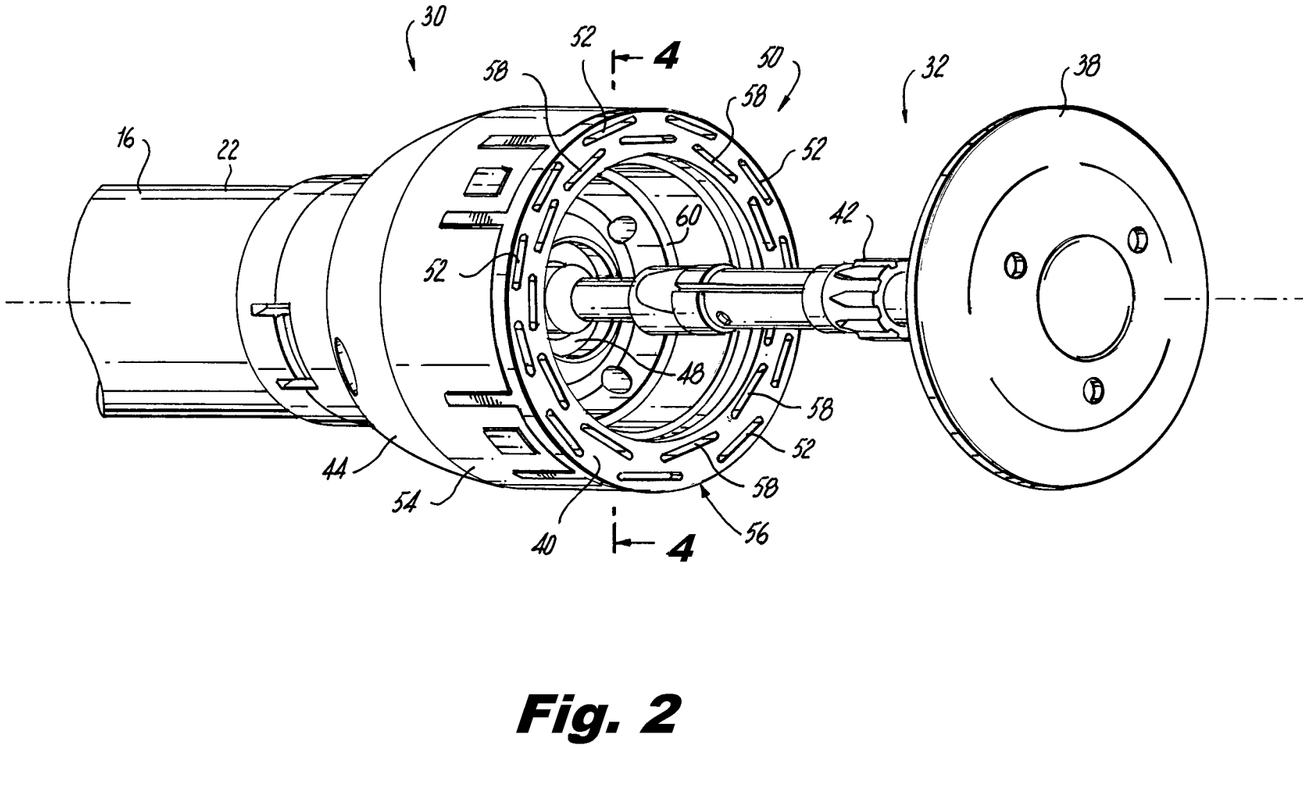
FIG. 2 is an enlarged perspective view of a distal head portion of the surgical stapling device.

Referring now to FIGS. 1 and 2, anvil assembly 32 includes a staple clinching anvil member 38. Shell assembly 30 has a staple guide 40 for guiding staples (not shown) out of shell assembly 30 and into corresponding staple clinching pockets (see FIG. 12) of the anvil member to staple tissue captured between the shell assembly 30 and anvil assembly 32, in a manner described in more detail hereinbelow. Upon actuation of firing trigger 26, staples (not shown) are ejected out of staple guide 40, through tissue and into staple clinching anvil member 38 to staple the tissue. Anvil assembly 32 additionally includes an anvil retainer 42 connected to anvil member 38 and movable in response to rotation of approximation knob 28 to draw anvil member 38 adjacent staple guide 40 and capture tissue there between.

With specific reference to FIG. 2, shell assembly 30 includes a shell 44 having an outer housing portion 46 and an inner guide portion 48 for removable receipt of anvil retainer 42. The staple guide 40 is mounted in the housing portion 46, and has one or more rows of staple pockets or slots. The staple guide 40 shown in FIG. 2 includes an outer circumferential row 50 of staple containing slots or pockets 52 adjacent a distal end 54 of shell 44 and an inner circumferential row 56 of staple containing slots or pockets 58 located radially inwardly of outer ring 50 of staple containing pockets 52. A cylindrical knife blade 60 (see FIG. 2) is located within shell assembly 30 and is also movable in response to actuation of firing trigger 26 to sever stapled tissue.

Figure 3:
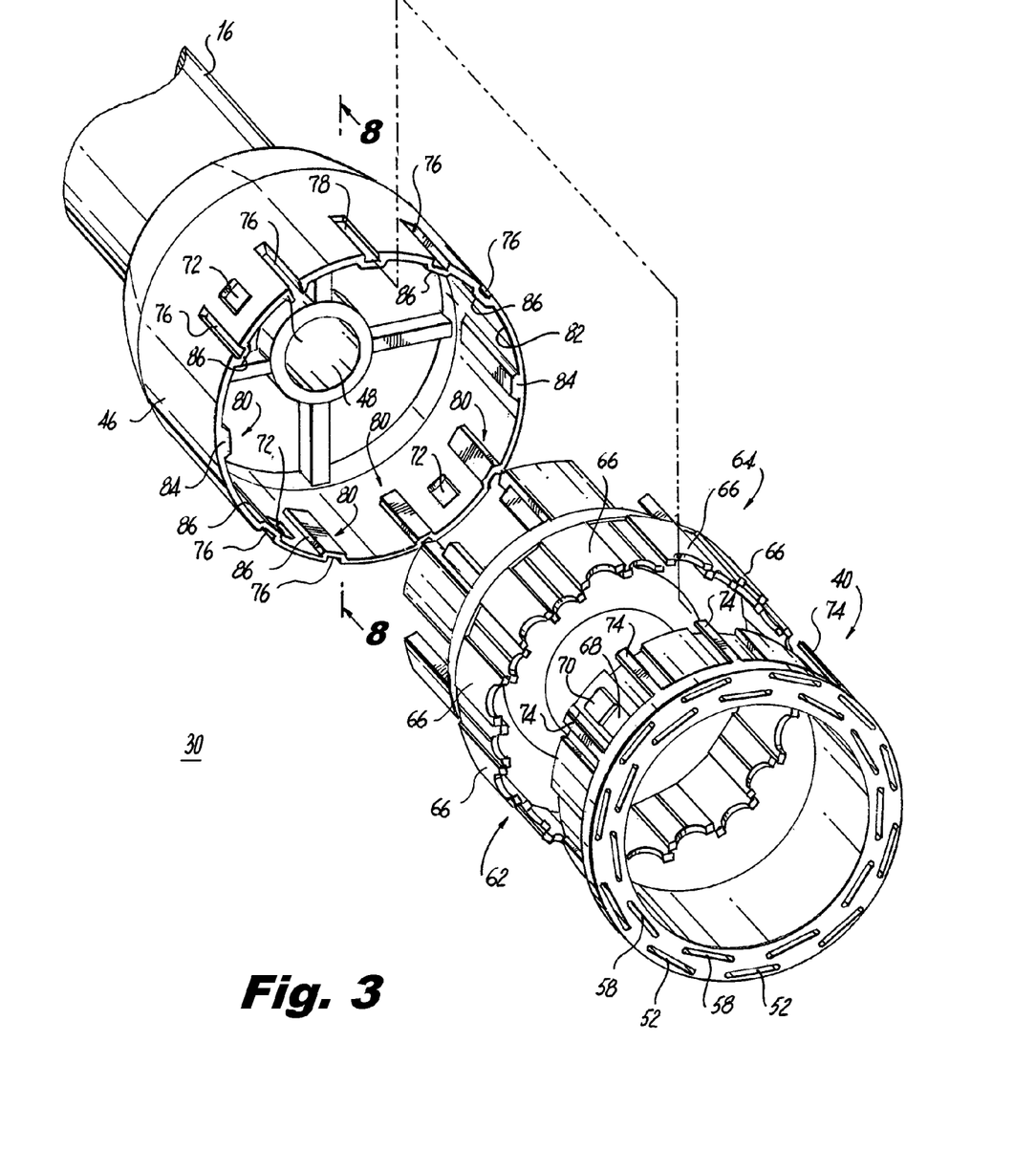
FIG. 3 is a perspective view, with parts separated, of a shell assembly of the distal head portion of the surgical stapling device.

Referring to FIG. 3, in order to eject staples (not shown) out of staple pockets 52 and 58, shell assembly 30 additionally includes a pusher back 62 positioned within shell 44 and proximal of staple guide 40. Pusher back 62 includes an outer row 64 of distally extending fingers 66 which are aligned with staple pockets 52 such that advancement of distally extending fingers 66 through staple pockets 52 forces staples into anvil member 38. Pusher back 62 additionally includes an inner row of distally extending fingers which are aligned with staple pockets 58 and similarly serve to eject staples into anvil member 38.

In order to retain pusher back 62 within shell 44 and secure a staple guide 40 to outer housing portion 46 of shell 44, staple guide 40 includes proximally extending arms 68 terminating in tabs 70 which engage notches 72 formed in outer housing portion 46. Proximally extending guides or fingers 74 extend from staple guide 40 and engage longitudinal guide slots 76, positioned on either side of notches 72, formed in outer housing portion 46. An additional longitudinal guide slot 78 is also formed in outer housing portion 46 and serves as a visual indicator to assist the user in orienting surgical stapling device 10.

Outer housing portion 46 is provided with a plurality of radially inwardly directed and longitudinally extending ribs 80 provided along an inner surface 82 of outer housing portion 46. Ribs 80 serve to strengthen outer housing portion 46 and allow outer housing portion 46 to have a minimal wall thickness as will be discussed in more detail hereinbelow. Forming outer housing portion 46 with a minimally structural permissible thickness allows outer and inner rows 50 and 56 of staple pockets 52 and 58, respectively, to have maximum radial dimensions thereby maximizing the diameter of the staple lines formed in tissue and permitting greater fluid flow through the stapled tissue.

Figure 4:
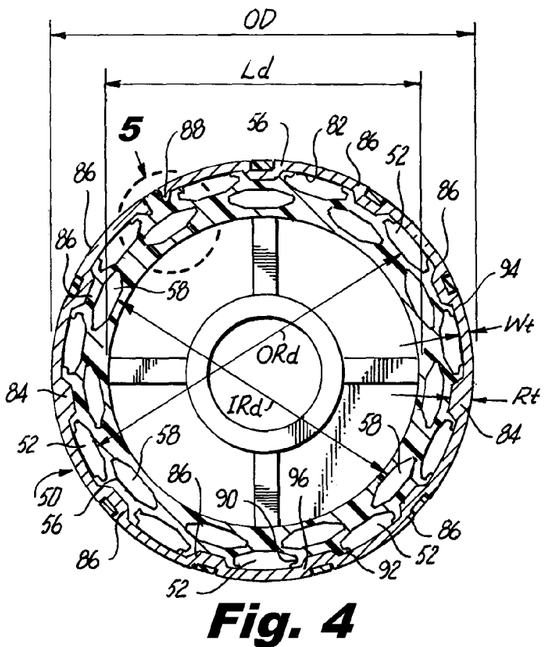
FIG. 4 is an end view of the shell assembly.
Figure 8:
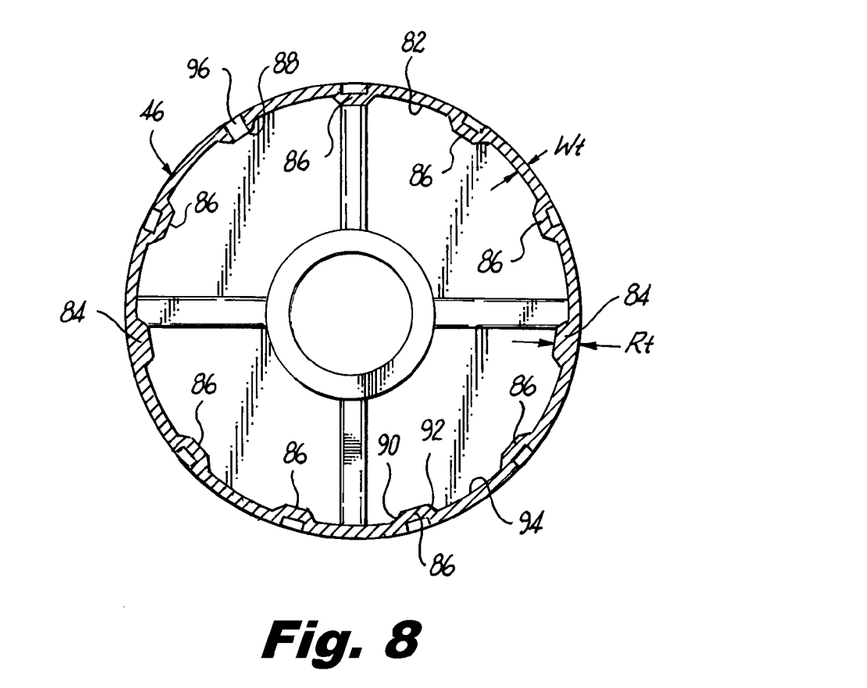
FIG. 8 is an end view of a shell of the shell assembly of FIG. 4.

With reference to FIGS. 3, 4 and 8, ribs 80 may include solid ribs 84, indented ribs 86 and/or bisected ribs 88. Solid ribs 80 may be formed integrally with inner surface 82 of outer housing portion 46 or may be affixed to inner surface 82 by various known methods such as, for example, gluing, welding, fusing, etc. For example, a plurality of ribs of the outer housing portion can be all solid ribs 84, all indented ribs, all bisected ribs, or a combination of various types of ribs. Indented ribs 86 may coincide with longitudinal slots 76 formed in outer housing portion 46 and may be formed by stamping, gluing, welding, fusing, etc. Bisected ribs 88 may be formed from solid ribs 84 or indented ribs 86 and include cuts completely through outer housing portion 46.

Referring for the moment to FIG. 8, ribs 80 are formed with angled sides 90 and 92 which taper inwardly from inner surface 82 of a wall 94 of outer housing portion 46 and have a rib thickness Rt. This strengthens wall 94 while allowing sufficient room for outer row 50 of staple slots 52 to be positioned as close as possible to inner surface 82 of wall 94. Locating the staple slots as close to the outer surface of the shell as possible expands the dimension of the anastomosis. As noted hereinabove, bisected ribs 88 include a cut or slot 96 formed through ribs 88 and wall 94.

Figure 5:
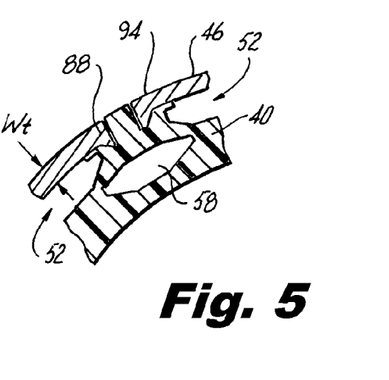
FIG. 5 is an enlarged area of detail view of the shell assembly of FIG. 4.

As best shown in FIGS. 4 and 5, outer housing portion 46 is formed with wall 94 having a relatively thin thickness Wt. Since the wall thickness Wt of wall 94 is less than the rib thickness Rt of ribs 80, outer housing portion 46 has a varying wall thickness. It should be noted that, while ribs 80 are illustrated as being generally trapezoidal in section, they may have other shapes such as, for example square, partially oval and in conjunction with inner surface 82 of wall 94 may form a sinusoidal or other varying wall thickness configuration.

Thus, shell assembly 30 is formed so as to provide a larger internal lumen diameter Ld relative to a given outer diameter OD of outer housing portion 46. By maximizing lumen diameter Ld, the resulting staple lines formed in tissue, and the area cored out by an associated knife blade, are of a maximum attainable diameter. This allows an increased fluid flow through the tissue that has been anastomosed, thereby making the resulting anastomosis between two tubular tissue sections approximate as closely as possible the pre-cut and sutured tissue structure.

With reference to FIG. 4, by forming wall 94 of outer housing portion 46 with a minimal thickness Wt, it allows outer row 50 of staple pockets 52 to have a maximum diameter ORd and inner row 56 of staple slots 58 to also have a maximum diameter IRd. Additionally, positioning or "nesting" staple pockets 52 of outer row 50 between adjacent ribs 80 further allows staple pockets to be as close as possible to inner surface 82 of wall 94. Additionally or alternatively, staple pockets 58 of inner row 56 are nested or positioned between adjacent staple pockets 52 of outer row 50 to maximize inner row diameter IRd. While not specifically shown, an associated cylindrical knife blade is also formed with a maximum allowable diameter for a given OD of outer housing portion 46. (Compare FIGS. 4 and 6). The housing portion and staple guide cooperate to provide sufficient rigidity for the assembly. Furthermore, any of the embodiments disclosed herein can include a pusher back that complements the ribbed outer housing portion of the shell, and also contribute to the rigidity of the distal head portion.

Figure 6:
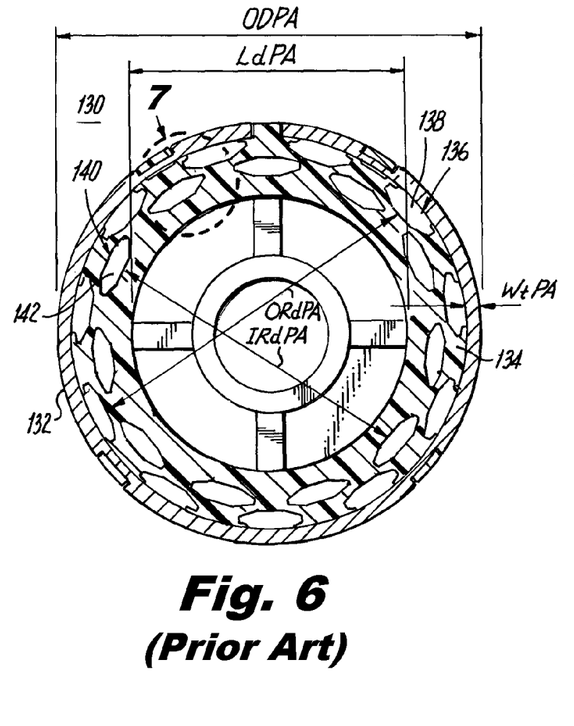
FIG. 6 is an end view of a prior art shell assembly.
Figure 7:
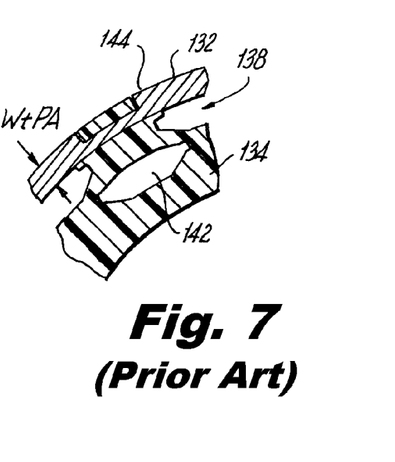
FIG. 7 is a an enlarged area of detail view of the prior art shell assembly of FIG. 6.
Figure 9:
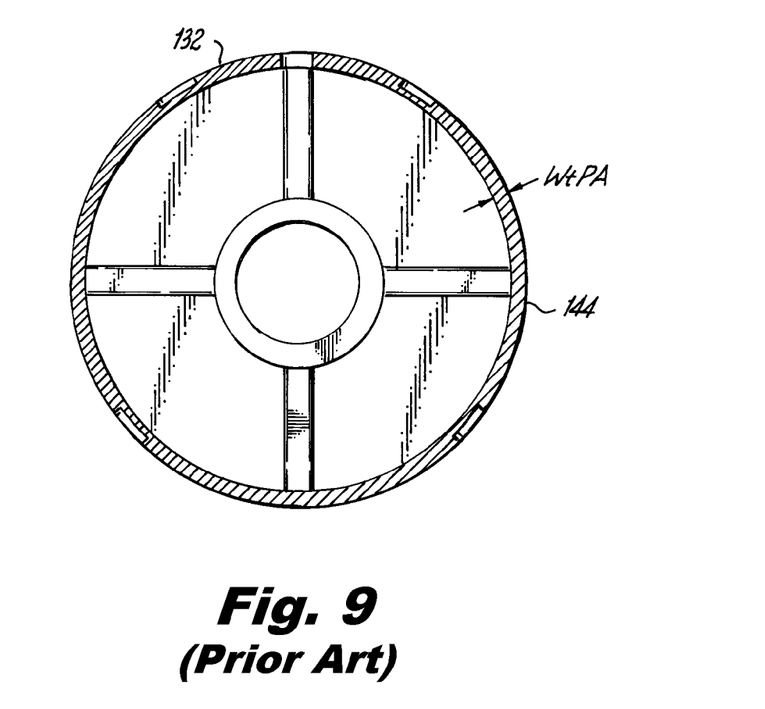
FIG. 9 is an end view of a prior art shell of the prior art shell assembly of FIG. 6.

Referring now to FIGS. 6, 7 and 9, and initially with respect to FIG. 6, there is illustrated a prior art shell assembly 130 of the type typically associated with prior art surgical stapling devices. Shell assembly 130 includes an outer housing portion 132 and a staple guide 134. Staple guide 134 includes an outer row 136 of staple pockets 138 having an outer row diameter ORdPA and an inner row 140 of staple pockets 142 having an inner row diameter IRdPA. As best shown in FIGS. 7 and 9, outer housing portion 132 of prior art shell assembly 130 has a wall 144 with a thickness WtPA.

Now with reference to FIGS. 4-9, for a given outer housing portion diameter, for example in the situation where outer diameter OD of outer housing portion 46 of the presently disclosed surgical stapling device 10 equals the outer diameter ODPA of the prior art outer housing portion 132 of a prior art surgical stapling device, the lumen diameter Ld of outer housing portion 46 is greater than, and maximized over, the lumen diameter LdPA of prior art outer housing portion 132. This is due to the thinner wall thickness Wt of wall 94 of outer housing portion 46 relative to the greater wall thickness WtPA of prior art outer housing portion 132. Outer row diameter ORd of outer row 50 is greater than outer row diameter ORdPA of prior art outer row 136 and inner row diameter IRd of inner row 56 is greater than IRdPA of prior art inner row 140. As noted hereinabove, the provisions of ribs 80 along the thinner inner surface 82 of outer housing portions strengthens wall 94 and provides the same or better structural integrity as that of greater thicker wall 144 of prior art outer housing portion 132.

For example, in a specific set of embodiments, the wall 144 thickness WtPa of prior art outer housing portion 132 is typically 0.0335 inches for a given outer diameter ODPA of outer housing portion 132. In a particular embodiment, wall thickness Wt of wall 94 is 0.0253 inches while rib thickness Rt of ribs 80 is 0.0435 inches where outer diameter OD of outer housing portion 46 is equal in diameter to outer diameter ODPA of prior art outer housing portion 132.

Figure 10:
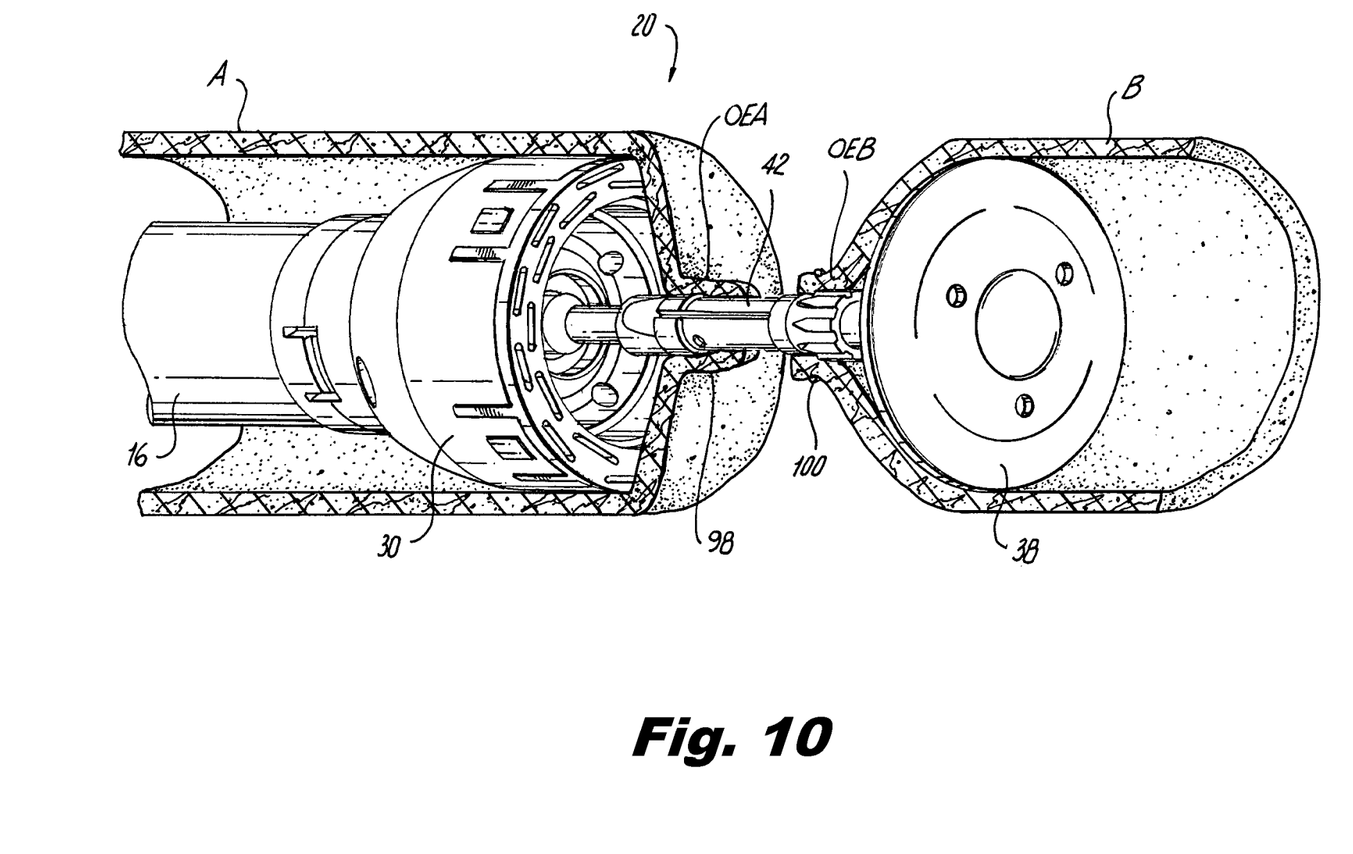
FIG. 10 is a perspective view, partially shown in section, of the distal head portion of the surgical stapling device of FIG. 1 positioned within a pair of tubular tissue sections prior to stapling.

Referring now to FIGS. 1 and 10-14, the use of surgical stapling device 10 to reconnect a pair of tubular tissue sections A and B will now be described. Referring initially to FIGS. 1 and 10, staple clinching anvil member 38 is initially an extended position relative to shell assembly 30. Distal head portion 20 of surgical stapling device 10 is inserted into a pair of tubular tissue sections A and B such that staple clinching anvil member 38 resides within tubular tissue section B and shell assembly 30 resides within tubular tissue section A. As best shown in FIG. 10, an open end OEA of tubular tissue section A is secured against anvil retainer 42 by a purse string suture 98 and an open end OEB of tubular tissue section B is secured against anvil retainer 42 by a purse string suture 100.

Figure 11:
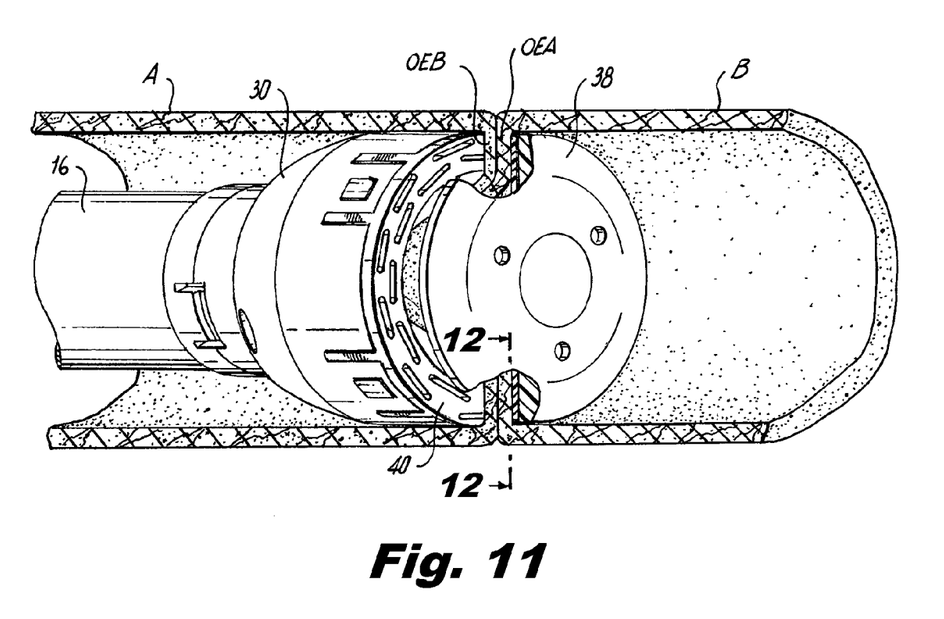
FIG. 11 is a perspective view, partially shown in section, of an anvil assembly of the distal head portion approximated against the shell assembly to approximate the pair of tubular tissue sections.

Referring to FIGS. 1, 10 and 11, rotatable approximation knob 20 on handle assembly 12 is rotated to draw anvil retainer 42, and thus staple clinching anvil member 38, proximally toward shell assembly 30. This clamps open end OEA of tubular tissue section A firmly against open end OEB of tubular tissue section B between staple clinching anvil member 38 and shell assembly 30. Once the user has received a visual indication via indicator 34 on handle assembly 12 that tissue sections A and B have been properly clamped by distal head portion 20, lock lever 36 is released and firing trigger 26 is compressed against stationary handle 24 to actuate surgical stapling device 10.

Figure 12:
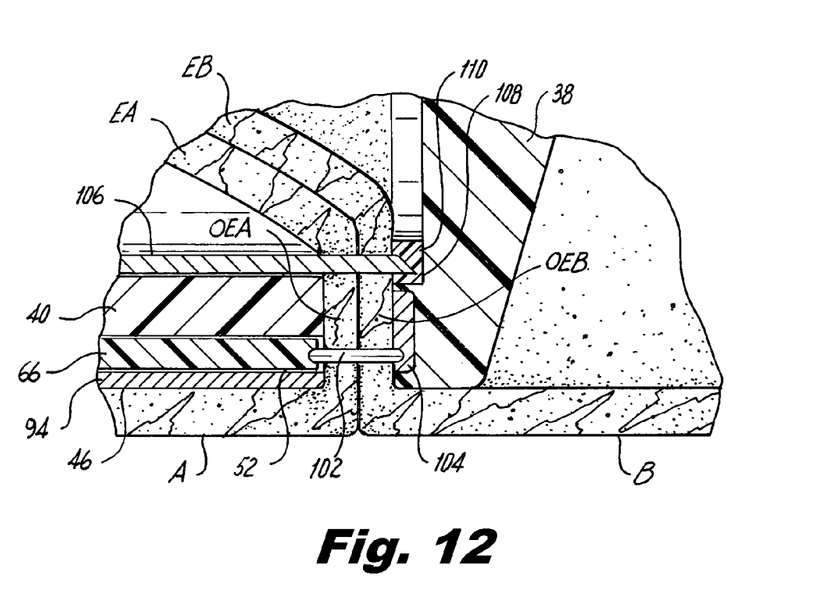
FIG. 12 is an enlarged, side cross-sectional view of a portion of the head assembly during stapling of the pair of tubular tissue sections.

With specific reference to FIG. 12, actuation of surgical stapling device 10 drives distally extending fingers 66 of pusher back 62 distally through a staple pockets such as, for example, staple pockets 52 in staple guide 40. Staples such as, for example staples 102, are driven out of staple pockets 52, through open end OEA of tubular tissue section A and open end OEB of tubular tissue section B and into staple clinching pockets 104 formed in anvil member 38. This securely staples open end OEA of tubular tissue section A to open end OEB of tubular tissue section B. While not specifically shown, simultaneously, additional staples 102 are driven out of staple pockets 58 of inner row of staple pockets 56 and into corresponding staple clinching pockets 104 formed in anvil member 38.

Figure 13:
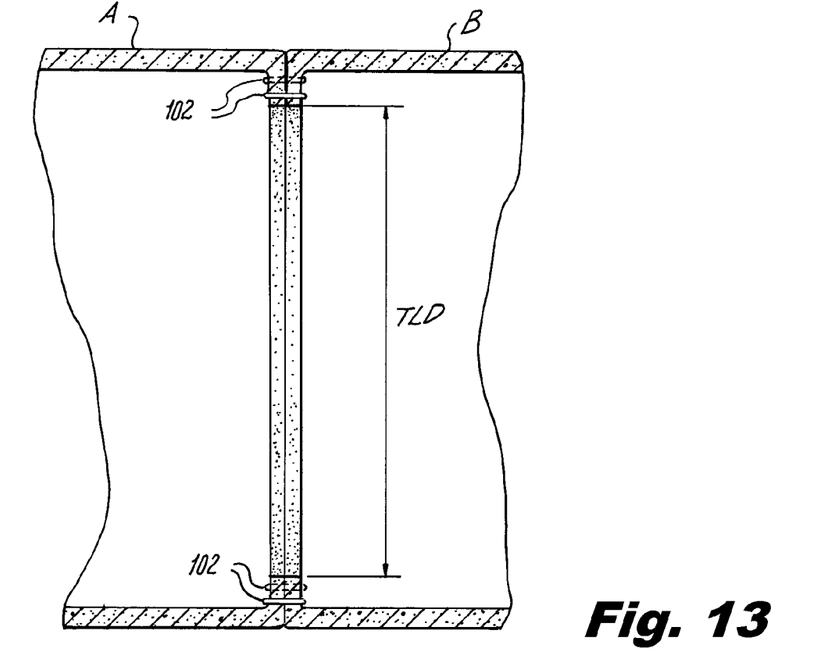
FIG. 13 is a cross-sectional view of the pair of tubular tissue sections after stapling by the surgical stapling device of FIG. 1.

Thereafter, a knife blade 106 is driven through tubular tissue sections A and B and into a backing ring 108 formed in anvil member 38 causing a sharp distal tip 110 of knife blade 106 to sever excess tissue EA and EB located radially inwardly of staples 102. As noted hereinabove, outer and inner rows of staple pockets 50 and 56, respectively, adjacent to the thin section of wall 94 of outer housing portion 46, the resultant secured tissue lumen diameter TLD is maximized (FIG. 13).

Figure 14:
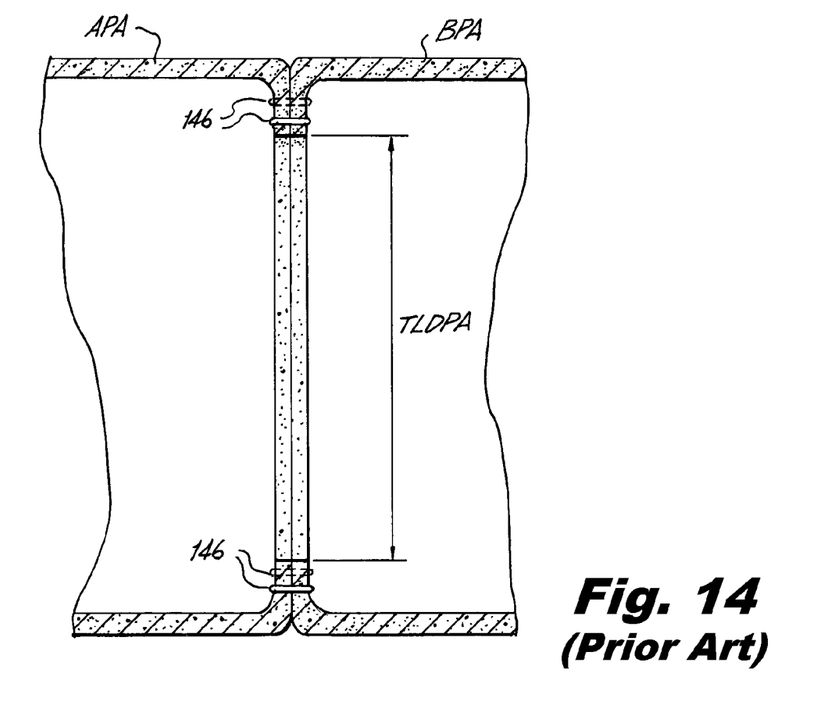
FIG. 14 is a cross-sectional view of a pair of tubular tissue sections after stapling by a prior art surgical stapling device incorporating the prior art shell assembly of FIG. 6.

Referring to FIG. 14, there is illustrated a pair of tubular tissue sections APA and BPA secured by prior art staples 146 of a prior art surgical stapling device. In this case, the joined prior art tissue lumen diameter is TLDPA. Referring to FIGS. 13 and 14, thus the use of surgical stapling device 10 results in a tissue lumen diameter TLD which is significantly greater than the tissue lumen diameter TLDPA provided by prior art surgical stapling device, thereby allowing greater fluid flow therethrough and promoting increased healing of the joined tissue sections.

It will be understood that various modifications may be made to the embodiments disclosed herein. For example, as noted here and above, the wall of the disclosed outer housing portion may have varying thicknesses. Further, the areas of increased and decreased wall thickness need not be identical but may vary individually depending upon the particular surgical procedures. Additionally, the disclosed areas of increased and decreased wall thickness need not be evenly spaced. Therefore, the above description should not be construed as limiting, but merely as exemplifications of particular embodiments. Those skilled in the art will envision other modifications within the scope and spirit of the claims appended hereto.

The invention claimed is:

1. A surgical stapling device comprising:
a handle assembly including a firing trigger;
a body portion extending distally from the handle assembly; and
a head portion disposed adjacent the body portion and including an anvil assembly and a shell assembly, the anvil assembly being movable in relation to the shell assembly between spaced and approximated positions, the shell assembly including:
an outer housing portion having a wall including areas of thinner and thicker wall thicknesses, wherein the areas of thicker wall thickness form longitudinally extending ribs extending along an inner surface of the wall of the outer housing portion; and
an outer row of staple pockets.

2. The surgical stapling device as recited in claim 1, wherein the outer row of staple pockets is located in the areas of thinner wall thickness.

3. The surgical stapling device as recited in claim 2, wherein the outer housing portion is cylindrical and the outer row of staple pockets is circular.

4. The surgical stapling device as recited in claim 1, wherein the ribs are solid.

5. The surgical stapling device as recited in claim 4, wherein the ribs are formed integrally with the wall of the outer housing portion.

6. The surgical stapling device as recited in claim 1, wherein the ribs are indented in the wall of the outer housing portion.

7. The surgical stapling device as recited in claim 1, wherein each rib is bisected by a slot.

8. The surgical stapling device as recited in claim 7, wherein each slot extends through each rib and the wall of the outer housing portion.

9. The surgical stapling device as recited in claim 1, wherein the ribs include angled sidewalls such that the ribs taper inwardly away from the inner surface of the wall of the outer housing portion.

10. A surgical stapling device comprising:
a handle assembly including a firing trigger;
a body portion extending distally from the handle assembly; and
a head portion disposed adjacent the body portion and including an anvil assembly and a shell assembly, the anvil assembly being movable in relation to the shell assembly between spaced and approximated positions, the shell assembly including:
a cylindrical outer housing portion having a wall including areas of thinner and thicker wall thicknesses, wherein the areas of thicker wall thickness form longitudinally extending ribs extending along an inner surface of the wall of the outer housing portion;
an outer ring of staple pockets aligned with the areas of thinner wall thickness, and
a pusher back movably mounted within the cylindrical outer housing portion for driving staples contained within the outer ring of staple pockets out of the outer ring of staple pockets and into the anvil assembly.

11. The surgical stapling device as recited in claim 10, wherein the pusher back includes longitudinally extending slots to accommodate the areas of thicker wall thickness.

12. The surgical stapling device as recited in claim 10, wherein the ribs are solid.

13. The surgical stapling device as recited in claim 10, wherein the ribs are indented in the wall of the outer housing portion.

14. The surgical stapling device as recited in claim 10, wherein each rib is bisected by a slot.

15. A method of increasing a lumen diameter of a pair of stapled tubular tissue sections comprising:
providing a surgical stapling device including:
an outer housing portion having areas of increased and decreased wall thicknesses, wherein the areas of increased wall thickness form longitudinally extending ribs extending along an inner surface of the wall of the outer housing portion;
an anvil member associated with the outer housing portion; and
a row of staple containing pockets disposed adjacent the areas of decreased wall thickness;
positioning the outer housing portion of the surgical stapling device within a first tubular tissue section;
positioning the anvil member of the surgical stapling device within a second tubular tissue section;
approximating the first tubular tissue section adjacent the second tubular tissue section; and
driving staples out of the row of staple containing pockets through the first and second tubular tissue sections and into the anvil member.

16. The method as recited in claim 15, further comprising severing excess tubular tissue of at least one of the first tubular tissue section or the second tubular tissue section with a cylindrical knife blade located adjacent the row of staple containing pockets.

* * * * *